United States Patent
Deng (10) Patent No.: US 6,740,293 B1
(45) Date of Patent: May 25, 2004

(54) HOUSING FOR TEST STRIP DEVICE AND TEST STRIP THEREFOR

(75) Inventor: Fangling Deng, Marlboro, NJ (US)

(73) Assignee: Biotech Atlantic, Inc., Eatontown, NJ (US)

( * ) Notice: Subject to any disclaimer, the term of this patent is extended or adjusted under 35 U.S.C. 154(b) by 276 days.

(21) Appl. No.: 09/906,962

(22) Filed: Jul. 17, 2001

(51) Int. Cl.$^7$ .............................................. G01N 33/48
(52) U.S. Cl. ......................... 422/58; 422/61; 436/164; 436/169
(58) Field of Search .............................. 422/56, 58, 61; 436/164, 169

(56) References Cited

U.S. PATENT DOCUMENTS

| | | | |
|---|---|---|---|
| 4,033,723 A | 7/1977 | Givner et al. .............. 23/253 R |
| 4,123,224 A | 10/1978 | Givner et al. ................. 422/59 |
| 4,208,187 A | 6/1980 | Givner ..................... 23/230 B |
| 4,774,192 A | 9/1988 | Terminiello et al. ......... 436/530 |
| 4,902,629 A | 2/1990 | Meserol et al. ............. 436/165 |
| 5,075,078 A | 12/1991 | Osikowicz et al. ........... 422/56 |
| 5,173,261 A | 12/1992 | Krause et al. ................ 422/58 |
| 5,223,219 A | * 6/1993 | Subramanian et al. ........ 422/55 |
| 5,356,782 A | 10/1994 | Moorman et al. ........... 435/7.9 |
| 5,602,040 A | 2/1997 | May et al. .................. 436/514 |
| 5,622,871 A | 4/1997 | May et al. .................. 436/514 |
| 5,656,503 A | 8/1997 | May et al. .................. 436/514 |
| 5,739,041 A | 4/1998 | Nazareth et al. ............ 436/518 |
| 5,916,522 A | * 6/1999 | Boyd et al. .................. 422/58 |
| 6,046,057 A | 4/2000 | Nazareth et al. ............ 436/514 |

* cited by examiner

Primary Examiner—Lyle A. Alexander
(74) Attorney, Agent, or Firm—Lerner, David, Littenberg, Krumholz & Mentlik, LLP (57) ABSTRACT

Testing devices for detecting a physical condition from a fluid specimen having, a housing movable from open to closed position for access to a test strip holding channel for a test strip, said housing has an enlarged end section for receiving the fluid to be tested thereon, with a plurality of serially disposed transverse channels on the exterior for catching fluid to be tested, an inlet port in each of said channels coacts with the test strip to enable the test strip to absorb a predetermined quantity of the fluid, and an outlet on said end section enables any excess fluid to overflow the end section. A sealing line when the housing is in the closed position has openings to prevent capillary action by the fluid from contaminating the test strip. A sealed viewing window on the housing enables the results by the test strip to be read.

20 Claims, 4 Drawing Sheets

HOUSING FOR TEST STRIP DEVICE AND TEST STRIP THEREFOR

BACKGROUND OF THE INVENTION

This invention relates generally to devices for assaying a condition in a human or animal such as pregnancy in a female which can be determined from body fluid such as urine and more particularly to a housing for such devices designed to control the flow of such body fluids on and across an enlarged exterior fluid sample receiving end of the housing, for establishing operative interrelation and engagement with an elongated test strip enclosed in the housing to control the quantity of the body fluid absorbed by the test strip, and for enhancing capillary flow along the test strip to a viewing window on the housing for viewing the positive or negative signal result on the test strip for the given test.

Single-use testing devices having a test strip therein for assaying a physical condition for humans and animals using body fluid, such as urine, by urinating thereon, by applying droplets of the body fluid thereon or by dipping the testing device in a quantity of the body fluid, are well known in the art, as is shown in pregnancy test devices of Abbott Laboratories covered by U.S. Pat. No. 5,075,078; of Carter-Wallace, Inc. covered by U.S. Pat. Nos. 5,739,041 and 6,046,057; and of Unilever covered by U.S. Pat. Nos. 5,602,040; 5,622,871 and 5,656,503; and also other U.S. Pat. Nos. 4,033,723; 4,123,224; 4,208,187; 4,774,192; 4,902,629; 5,173,261 and 5,356,782. These prior art patents show two basic types of pregnancy testing devices to which urine is applied. In one type the urine is applied to an exposed wick or specimen receiving end of the test strip. While good absorption of the fluid specimen is obtained by this type device, in order to achieve the desired operation and signal from the test strip, the device has many parts which increase the cost of assembly of these highly competitive products. In the other type of device the test strip is enclosed in the housing when the fluid sample is applied and flowed into the housing. Any unwanted hydraulic flooding which occurs produces improper and inaccurate signaling by the test strip on the result of a given test. Additionally, this second type of the test device also requires a plurality of parts and complex assembly which increases the cost per single-use device. Further, the prior art patents show that both of these type devices have relatively small impingement areas for the urine or fluid being tested and, as above indicated, pass high quantities of the fluid being tested into the housing for the respective test devices which produces unwanted hydraulic flooding and fluid pressures inside the test devices and tends to cause both improper chemical reactions and increased errors in the signals produced by and/or viewed in such testing devices.

The present invention overcomes these and other problems by providing a single-use testing device particularly adapted for detecting a physical condition such as pregnancy from a urine stream or specimen applied to the device in which a generally narrow elongated housing is particularly designed for holding and providing access to an elongated test strip disposed in the housing. The generally narrow elongated housing has an enlarged sample or specimen capturing or receiving area or section at one end which is shaped on the front surface and the rear surface of the housing with a plurality of serially disposed guide vanes with inlet ports or openings as hereinafter described disposed in their respective medial sections. The guide vanes and channels collect and pass the fluid to be tested which is brought into contact with or impinges on the enlarged specimen receiving section, through the medially disposed inlet openings, for contact and absorption by a test strip disposed along the longitudinal line in the housing and operatively disposed at one end for intimate engagement and coaction with the inlet openings in the enlarged specimen receiving end section of the housing. The inlet openings and the end of the test strip extending into the enlarged specimen receiving end section of the housing are operatively associated for engagement so that only a predetermined quantity of the fluid being tested is absorbed by the associated and coacting end of the test strip. The enlarged sized and shaped specimen receiving end section of the housing is further designed so that excess fluid to be tested or urine will overflow this end of the housing. The predetermined quantity of fluid or urine absorbed by the associated and coacting end of the test strip then travels by capillary action to a reaction portion on the test strip remote from the specimen receiving absorption end of the test strip, to a point for signaling the result, if any, of the physical condition on the given test. This signal can be detected through a window provided in the housing remote from the said enlarged specimen receiving end section on the housing. The housing is further designed with means to inhibit capillary action along joinder edges thereon to maintain the integrity of each test and has means therein to position, hold and protect the integrity of the test strip and to reduce excess moisture in the interior of the housing so as to insure proper directional capillary movement in the test strip of the fluid being tested and the accuracy of the test results.

It is another aspect of the present invention to provide a single-use testing device for detecting physical conditions from a fluid specimen or stream, such as urine applied thereto, having a housing movable from open to closed position to provide access to a test strip holding channel formed in and along the longitudinal line of the housing for holding an elongated test strip when the housing is in the closed position, said housing is enlarged, shaped and sized at one end to provide a specimen receiving area or section on the exterior of the housing for the fluid specimen or stream to be tested, an elongated handle section connected and continuous with one end of the enlarged specimen receiving end section has a sealed viewing window formed therein a spaced distance from the enlarged specimen receiving end section so that an elongated test strip, when mounted in the test strip holding channel, can extend from the enlarged specimen receiving end section through the housing past the viewing window, thus that the end of the elongated test strip in the enlarged specimen receiving end section can receive the sample quantity of the fluid specimen to be tested and transport the sample by capillary action past the viewing window in the handle, and the handle has venting means and desiccant means disposed relative the viewing window to prevent blurring of the window, collection of moisture and backflow of the sample so as to maintain the direction of capillary flow through the test strip when the test device is being used.

It is another aspect of the present invention to provide an improved structure and operation for a testing strip for use in a single-use testing device as above described consisting of an elongated multi-layered member sized to fit into a test strip holding channel formed on the housing for the testing device which has a base layer formed from a plastic film material on which a plurality of coacting and interrelated members or layers of absorbent and microporous materials are assembled and affixed to the base layer and/or to each other to provide a test strip having, an elongated sample collection end of highly absorbent material disposed when the test strip is in assembled position in the housing for operative engagement and coaction with the inlet ports or openings in the guide channels in the enlarged sized and shaped specimen receiving end section of the housing for easy absorption and saturation of a predetermined quantity of fluid or urine which is permitted to pass through the inlet ports or openings for contact with and absorption by the sample collection end of the test strip and for transport by capillary action of the absorbed fluid sample being tested to a reagent section for mixing a dried chemical reagent therein with the sample of the fluid specimen to be tested and to further transport this mixture to an intermediate section made of a microporous membrane which is in turn connected to an after-sol member made of a highly absorbent paper material. The intermediate section of the test strip extends past the sealed viewing window in the housing to signal the result of the test, if any, of the physical condition for which the test is being made and the after-sol pad continuous with the intermediate section further extends beyond the viewing window for communication with venting means and desiccant means in the housing to improve and maintain the proper directional capillary movement of the fluid being tested so the signal appearing in the viewing window will be accurate.

SUMMARY OF THE INVENTION

Thus, it is one aspect of the present invention to provide generally single-use testing devices for detecting physical conditions from a fluid specimen or stream such as urine applied thereto having, a housing movable from open to closed position to provide access to a test strip holding channel formed in the housing for holding a test strip made of absorbent and microporous materials when the housing is in the closed position, said housing is enlarged, shaped and sized at one end for receiving on the exterior of the housing the fluid specimen or stream to be tested, said enlarged specimen receiving end section has a plurality of serially disposed transverse guiding channels formed on at least one outer face of the housing. An inlet port or opening is formed medially in each of said transverse guiding channels and each of said plurality of inlet ports or openings is adapted for operative engagement and coaction with the sample collection end of the test strip mounted in the test strip holding channel to enable a predetermined quantity of fluid such as urine to be absorbed by to the sample collection end of the test strip. An overflow outlet on said enlarged end section is provided so that excess urine will flow off the enlarged specimen receiving end section of the housing, sealing means is formed along the joint closure line when the housing is in the closed position, including means to stop capillary action along the sealing means and prevent excess fluid or urine from entering the housing and contaminating the test strip in the strip holding space, and a sealed viewing window on said housing is provided for reading the reaction, if any, produced on the test strip from the absorbed fluid or urine sample being tested.

It is another aspect of the present invention to provide a test strip having absorbent and microporous materials for a single-use testing device in accordance with the present invention consisting of an elongated multi-layered member sized to fit into a test strip holding channel formed in the housing for the testing device which includes, a base layer formed from a plastic film material on which a plurality of additional members, elements or layers of absorbent and microporous materials are connected to the base layer and to each other in overlapping relation to provide an elongated sample collection member disposed for operative engagement and coaction in the enlarged specimen receiving end section in the housing to absorb and transport by capillary action a sample of the fluid to be tested, to a reagent section for mixing the dried testing chemical therein with the fluid sample to be tested and to pass it to one end of an intermediate microporous membrane extending through the housing connected at the opposite end to an after-sol absorbent pad, the intermediate microporous membrane which passes across the sealed viewing window to signal the result of the test, and the after-sol absorbent pad extends beyond the sealed viewing window for communication with the venting and desiccant means to enable the capillary action to continue through the test strip and insure that the signal provides an accurate reading in the viewing window for the fluid sample being tested.

It is another aspect of the present invention to provide a testing device having a housing with a lower shaped section and a coacting matching shaped upper section having means for generally sealing the upper and lower sections to each other to define a test strip receiving space therein when in the closed position and means on said housing to prevent capillary flow of fluid or urine contacting the outside of the housing along the means for sealing the upper section and lower section when in the closed position to increase the accuracy of the results obtained by the testing device and to prevent a person's hands from being contaminated when urine impinges on the enlarged specimen receiving end section of the housing.

It is another aspect of the present invention to increase the accuracy of the results obtained by the testing device in accordance with the present invention by providing means to allow the fluid or urine impinging on the exterior of the test device to overflow without affecting the control of the predetermined quantity of fluid or urine which is absorbed by the coacting test strip in the housing.

It is another aspect of the present invention to provide vent means on the housing in communication with the interior to allow excess moisture to escape from the housing, prevent backflow of the fluid being tested along the test strip, to improve operation of the test strip therein, and also to prevent the viewing window from becoming blurred.

It is another aspect of the present invention to provide a desiccant in the housing to absorb moisture collected in the housing when the test device is not in use.

It is still another aspect of the present invention to provide in a testing device a test strip receiving channel, operative at one end to contain the test strip when placed therein for operative coaction with inlet openings or ports in the enlarged specimen receiving end section to control the quantity of fluid to be tested which is absorbed by the operatively engaging and coacting sample receiving end of the test strip in engagement with the inlet ports or openings in such assembled position, to prevent fluid from entering the housing, and to easily establish and continue movement of the fluid being tested by enabling the capillary action to continue when the test device is in use.

It is a further aspect of the present invention to provide in a testing device a longitudinally extending test strip receiving channel in and along the housing for removably receiving an elongated test strip therein which extends from the enlarged specimen receiving end section past the viewing window and for contact with protruding members on the inner wall of the housing for holding the test strip in assembled position in the test strip receiving channel.

It is a still further aspect of the present invention to provide in a testing device having a housing with an enlarged specimen receiving section at one end for contact with a fluid to be tested such as urine, guide channels and inlet ports for the fluid to be tested, on said enlarged specimen receiving end section, a viewing window remote from the enlarged specimen receiving end section for signaling the results of the test of such fluid, venting openings on the side of said window viewing section opposite from the enlarged specimen receiving end section, and a longitudinally extending test strip receiving channel in and along the longitudinal line of the housing for receiving an elongated test strip made of absorbent and microporous materials in operative engagement at one end with the inlet ports in said enlarged end section to control by the absorption as a function of the materials the quantity of fluid to be tested and the opposite end of said test strip extending beyond the viewing window to enable absorbed fluid being tested to vaporize through vent openings in the housing so movement by capillary action of the absorbed fluid in the test strip is maintained and will continue, and backflow of absorbed fluid in the test strip is prevented. While the test strip has an operative interrelation with the inlet ports or central openings in the guide channels of the enlarged end sections, those skilled in the art will recognize that such test strips are well known to those skilled in the art.

BRIEF DESCRIPTION OF THE DRAWINGS

With these and other objects in mind, the present invention will now be described in more detail with reference to the accompanying drawings in which.

DETAILED DESCRIPTION

Referring to the drawings, FIGS. 1 to 6 of the drawings show the test device generally designated 10 in accordance with the present invention having an elongated, sized and shaped housing 11 preferably made of a suitable type of plastic such as polyethylene and polypropylene which is inert chemically to the fluids which will be directed onto the outer surface of the housing 11. Housing 11 is formed by a first shaped lower section 12 and operatively connected second shaped and matching upper section 13 connected to each other by a plastic living hinge 14 so they can be pivoted from open to closed position and vice versa. Conventional spaced connecting members as at 11a and 11b are also provided at spaced locations along the housing to enable the lower section 12 and upper section 13 to be snapped and held securely to each other in the closed position. These devices are well known in the art as closures for interengaging plastic members and therefore will not be more fully described as they function for the same purpose on the housing 11 for testing device 10. While the first lower section and matching second upper section are shown as pivotally connected to each other, those skilled in the art will recognize that the first section and second section can be connected without the necessity of a hinge and that such hinge is merely a convenient device for maintaining these sections of the housing together.

When the first shaped lower section 12 and second shaped matching upper section 13 are in the closed position, housing 11 in plan view is shown to have an enlarged shaped and sized section at one end to define on the exterior of both the lower section 12 and upper section 13 a contact, impingement or specimen receiving end section 15 for the fluid specimen or stream to be tested, such as urine, by the test device 10. The enlarged shaped and sized specimen receiving end section 15 is at least twice as wide as handle section 16 of the housing 11 and will have a length to provide a contact, impingement or specimen receiving area of at least four times greater than existing prior art devices. More specifically, the width of the enlarged specimen receiving end section 15 will be about 17 mm, the width of the handle section at its widest point will be about 15 mm, the length of the enlarged specimen receiving end section will be about 35 mm, and the length of the elongated handle will be about 95 mm. Those skilled in the art will recognize that these dimensions can be varied in relative ratios to each other without departing from the scope of the present invention. The elongated handle section 16 is connected to the inner end of the enlarged impingement or specimen receiving end section 15 and extends in the longitudinal line of the housing 11 continuous from the enlarged end section 15. However, because the enlarged end section 15 is relatively wider than the handle section 16, a connection or junction section as at 17 is formed between the enlarged end section 15 and the handle section 16, all of which is shown by FIGS. 1 to 6 of the drawings.

The interior of lower section 12 and upper matching section 13 of the housing 11 are formed and shaped to define and provide a test strip receiving and holding channel generally designated 18 in which a test strip 19 can be removably mounted when the lower section 12 and upper section 13 are moved to the open position. While it is possible when the lower section 12 and upper section 13 are in the open position to remove a used test strip 19 and replace it with a fresh unused test strip, this will not enable the test device to be reused again. The test device after each use is contaminated, it cannot be reused by merely placing a fresh unused test strip therein. Before the test device 10 can be reused, it must be thoroughly cleaned and sterilized. Thus, in the commercial marketplace and in actual practice, the test device 10 is used as a single-use test device because of relatively low cost of such devices and the inconvenience which attaches to decontaminating and sterilizing the housing before it can be reused.

Figures 1, 2, 3, 4, 5, 6:
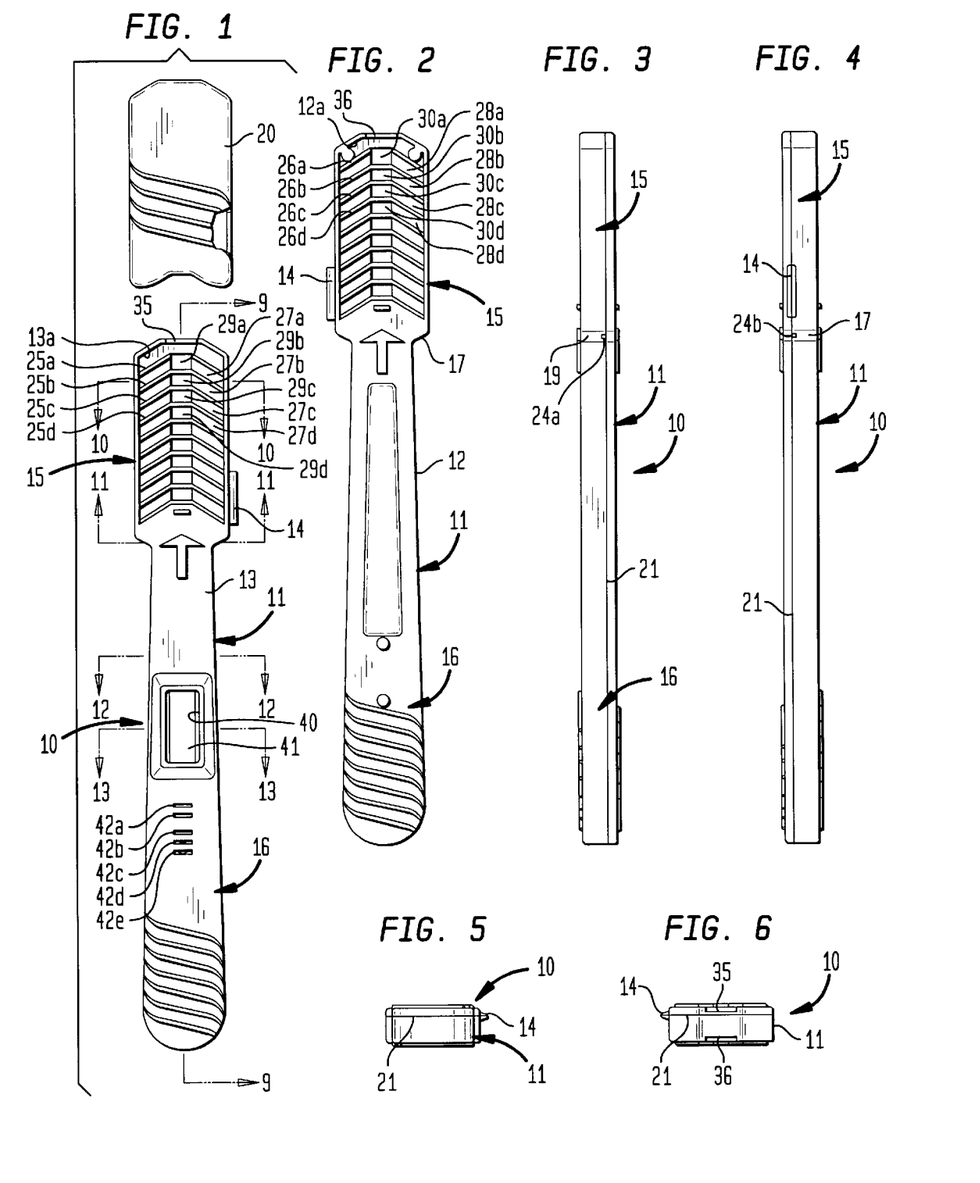
FIG. 1 is a top plan view of the housing for a test device in accordance with the present invention in the closed position, showing the cover for the fluid specimen receiving end section.
FIG. 2 is a bottom plan view of the housing without the cover for the test device as shown in FIG. 1.
FIG. 3 is a right side view of the housing for a test device as shown in FIG. 2.
FIG. 4 is a left side view of the housing for a test device as shown in FIG. 2.
FIG. 5 is a view of the handle end of the housing for a test device as shown in FIG. 2.
FIG. 6 is a view of the enlarged end section of the housing for a test device as shown in FIG. 2.

A cover 20 is provided for the enlarged shaped and sized contact, impingement or specimen receiving section 15 to reduce contamination of the specimen receiving section when the test device is not in use. When the test device 10 is ready for use, cover 20 is removed as is shown at FIG. 1 of the drawings. After the test device is used or when observing the test results, the cover 20 is replaced to prevent the now used test device from soiling or leaving excess body fluids on any surface where the test device 10 may be placed.

Referring to FIGS. 1–6, 7, 8, 9 and 10, the elongated lower section 12 and matching upper section 13 are formed for interengagement with each other so as to generally seal the interior of the housing at the joint or closure line 21 which extends around the housing 11 when the lower section 12 and upper section 13 are snapped to the closed position. Thus, an indented shoulder as at 22 extends substantially around and inwardly along the entire periphery of lower section 12, and a protruding lip as at 23 extends substantially around and inwardly along the entire periphery of upper section 13. The respective shoulder 22 and lip 23 are disposed substantially the same distance inwardly and are so shaped and sized that when the lower section 12 and upper section 13 are snapped to the closed position, the coacting shoulder 22 and lip 23 will come into engagement with each other to form the generally fluid tight seal.

As will be understood by those skilled in the art, despite the formation of a generally fluid tight seal at the joint or closure line 21, fluid such as the urine sample or specimen which contacts or impinges on the enlarged specimen receiving end section 15 of the housing 11 has the capacity to creep by capillary action across this joint or closure line. If such fluid is permitted to enter the handle section 16 of housing 11 and contacts the test strip 19, it will affect the accuracy of the test results signaled by test strip 19. Accordingly, at the junction section 17 between the enlarged shaped and sized end section 15 and handle section 16 of the housing 11, the respective shoulder 22 and lip 23 are broken to form openings as at 24*a* and 24*b* respectively on opposite sides of the junction section 17 of the housing 11 and during use of the test device 10 prevent such fluid or urine from creeping by capillary action past junction section 17 along closure line 21 onto the handle section 16. This also prevents excess body fluid being tested from wetting and contaminating the hand of the user of the test device 10.

At the sized and shaped contact, impingement or specimen receiving end section 15, the housing is designed to permit a predetermined quantity of the fluid to be tested by contact and absorption by the test strip 19 and also to permit any excess of such fluid to overflow and escape off the exterior of the specimen receiving end section 15.

Enlarged sized and shaped contact, impingement or specimen receiving end section 15 of the housing 11 is shown as having a generally octagon shape in plane view which is elongated along the opposite side walls 15*a* and 15*b*. Those skilled in the art will recognize that this shape for the enlarged end section 15 was selected because it is adapted for the further design of the end section now to be described.

Therefore the end section 15 may have many other convenient and functional shapes without departing from the spirit and scope of the present invention. Further, on the exterior surfaces of each of the respective lower section 12 and coacting upper section 13 of the housing, the enlarged sized and shaped contact, impingement or specimen receiving end section 15 has serially spaced and transversely disposed partitions or walls as at 25*a*, 25*b*, 25*c* and 26*d*, etc. on the upper section 13 and similarly at 26*a*, 26*b*, 26*c* and 26*d*, etc. on lower section 13. Formed between each pair of partitions or walls are transversely disposed guide channels as at 27*a*, 27*b*, 27*c* and 27*d*, etc. in upper section 13, and similarly transversely disposed guide channels at 28*a*, 28*b*, 28*c* and 28*d*, etc. in lower section 12, all of which is shown in FIGS. 1, 2, 9 and 10 of the drawings. The transverse partitions 25*a*, 25*b*, 25*c* and 26*d*, etc. and their associated transverse guide channels 27*a*, 27*b*, 27*c* and 27*d*, etc. in the upper section 13 and transverse partitions 26*a*, 26*b*, 26*c* and 26*d*, etc. and their associated transverse guide channels 28*a*, 28*b*, 28*c* and 28*d*, etc. in lower section 12 will be so sized that they will trap a predetermined amount of fluid when the fluid to be tested is brought into contact or impinges on the enlarged specimen receiving end section 15. The partitions also have a geometric design to aid and to guide movement of trapped fluid to be tested toward the medial section of the associate and similarly shaped transverse guide channels formed between the partitions as above described to pass the fluid to inlet ports or openings as hereinafter described.

Thus, when the housing is in the closed position each of the respective transversely disposed guide channels are provided with inlet ports or openings as at 29*a*, 29*b*, 29*c* and 29*d*, etc. for channels 27*a*, 27*b*, 27*c* and 27*d* in the upper section 13 and inlet ports or openings as at 30*a*, 30*b*, 30*c* and 30*d*, etc. for channels 28*a*, 28*b*, 28*c* and 28*d* in the lower section 12. These inlet ports or openings communicate with the interior of the housing 11, all of which is shown by FIGS. 1, 2, 7, 8, 9 and 10 of the drawings.

However, the drawings also show that the fluid to be tested does not and cannot flood into the interior of the housing 11 because the respective inlet ports or openings are occluded by and are in operative engagement and coaction with the test strip 19 itself so that the actual quantity of the fluid to be tested which reaches the test strip is a function of the size of the inlet ports or openings, of the absorption characteristics of the materials from which the test strip 19 is formed and of the capillary action in the test strip as the fluid being tested moves therethrough during use of the test device 10.

This advantageous operative interengagement between the inlet ports or openings and the test strip 19 is achieved by providing in the lower section 12 longitudinally extending partially L-shaped partitions 31 and 32 which are spaced from each other a distance equivalent to the width of the test strip 19 and are disposed on opposite sides of the inlet ports or openings 30*a*, 30*b*, 30*c* and 30*d*, etc. Generally L-shaped partition 31 is connected at one end to the interior of end wall 12*a* of the lower section 12 and at the opposite end to the associated side wall 15*a* of the shaped enlarged end section 15. And similarly the generally L-shaped partition 32, at a spaced distance from L-shaped partition 31, is also connected to the interior of end wall 12*a* and to the associated opposite side wall 15*b* of the shaped enlarged end section 15. Since the L-shaped partitions 31 and 32 are on opposite sides of the inlet ports or openings 30*a*, 30*b*, 30*c* and 30*d*, etc. in the lower section 12 of the housing 11, they form a portion of the test strip receiving channel 18, and this allows the elongated sample receiving end 19*a* of the sized test strip 19 to be fitted snugly into position between the spaced L-shaped partitions 31 and 32 so that the test strip occludes openings or ports 30a, 30b, 30c and 30d.

The test strip 19 will also occlude openings or ports 29a, 29b, 29c and 29d, etc. in the upper section 13 because the portion of the interior of the end section 15 on the upper section 13 of the housing having the openings 29a, 29b, 29c and 29d, etc. is in the form of a block-like section as at 15c so sized that when the upper section 13 is snapped to the closed position, the block-like section 15c will fit partially into the space between the L-shaped partitions 31 and 32 leaving enough room for, but disposed in engagement with, the upper face of the sample receiving end 19a of the test strip 19 so that the openings 29a, 29b, 29c and 29d, etc. are also occluded, and the fluid to be tested will not flood through the inlet ports or openings into the housing 11, all of which is shown by FIGS. 1, 2, 7, 8, 9 and 10 of the drawings.

Thus, the contact, impingement or specimen receiving end section 15 and the sample receiving end of the test strip receiving channel 18 are so constructed that when the test strip 10 is in assembled position in the test strip receiving channel 18, the test strip will only receive a predetermined quantity of the fluid to be tested as a function of the size of the inlet ports or openings, the ability of the test strip to absorb the fluid to be tested with which it comes in contact and the capillary action achieved in the test strip when the testing device 10 is in use.

The enlarged specimen receiving end section 15 is also provided with lateral disposed collection spaces 33 and 34 outward of the blocklike section 15c which communicate with the openings 24a and 24b. These collection spaces 33 and 34 also prevent any of the fluid to be tested which gets into the interior of the enlarged end section 15 of the test device 10 from acting to cause the fluid being tested from flowing through the test strip 19 in the wrong direction or from passing into the housing 10 by moving under the test strip 19 in its assembled position in the test strip receiving channel 18 in the enlarged specimen receiving end section 15 and the housing 11.

FIGS. 1, 2, 6 and 9 also show that an upper outlet or relief opening 35 is provided in the end wall 13a of the upper section 13 and a lower outlet or relief opening 36 is provided in the end wall 12a of the lower section 12 to enable the excess fluid to be tested which is brought into contact with the contact or impinging end section 15 to flow freely off of the end section 15 to prevent increasing the hydraulic pressure in the fluid to be tested as it contacts the sample receiving end of test strip 19 as above described.

The remaining sections of the test strip receiving channel 18 extend from the enlarged end section 15 into the handle section 16 of the housing 11, where the lower section 12 and upper section 13 of the housing coact to hold the test strip 19 in the test strip receiving channel 18. Thus, along the interior wall of the lower section 12 generally continuous with the sample receiving section 18a of the strip receiving channel 18, there is a flat section 18b which extends longitudinally along the floor of the interior of lower section 12 past spaced guide members 37a and 37b disposed respectively on the opposite side walls 12b and 12c of the lower section 12. Guide members 37a and 37b are spaced apart the same width as the elongated test strip 19 and hold the test strip in position for viewing the test result signaled by the test strip during use of the test device 10. The flat section 18b continues past the spaced guide members 37a and 37b to a stop member 38 which coacts with the end wall 12a of the lower housing to prevent the test strip from sliding longitudinally when in assembled position in the test strip receiving channel 18. The test strip is also held in assembled position in the test strip receiving channel 18 by a plurality of spaced projections 39a, 39b, 39c and 39d along the interior of the handle end of upper section 13 of housing 11 between the end section 15 and a window section 40 formed in the upper section 13 for viewing the results signaled by the test strip 19 during the use of the test device 10.

Window section 40 is approximately the same width as the test strip and will have a length sufficient to view enough of an intermediate signal. section 19c on the test strip 19 to see the reaction results, if any, signaled by the intermediate signal section 19c during the use of the test device 10. Window section 40 includes a clear plastic pane 41 so secured in the window section 40, as is shown in FIGS. 1, 7, 9 and 13 of the drawings that the window section is sealed to prevent the fluid being tested or urine on the exterior of the test device 10 from entering the interior of the housing 11 to contaminate the test strip and render the results of the testing device 10 inaccurate.

Figure 7:
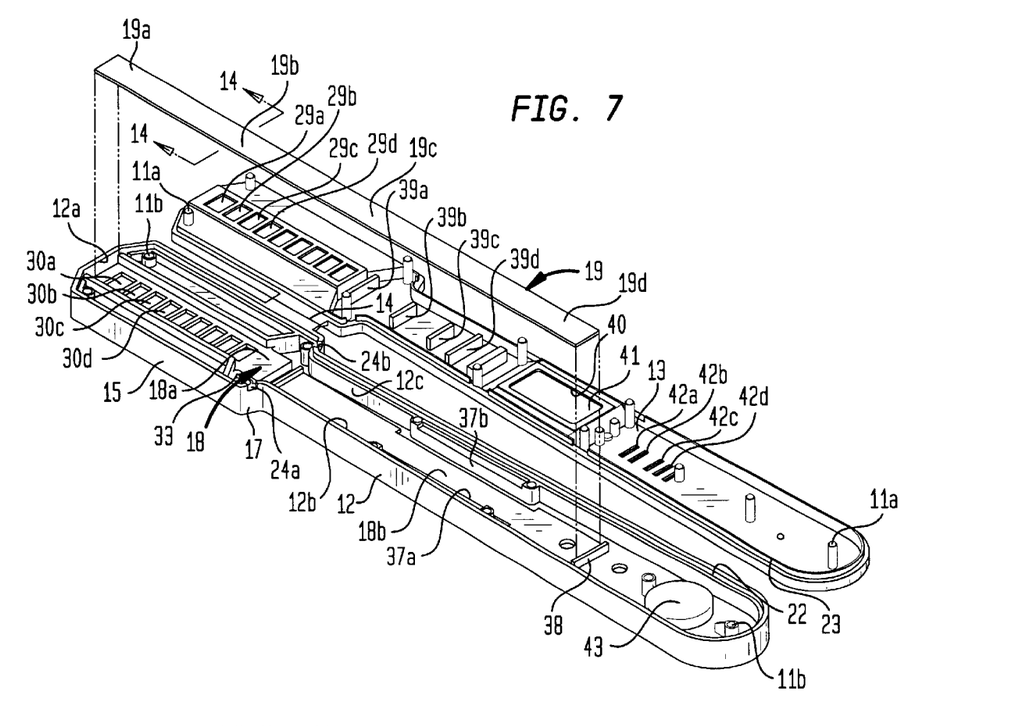
FIG. 7 is a perspective view of the housing for a test device as shown in FIG. 2 in the open position with the test strip exploded from the test strip holding channel.
Figure 8:
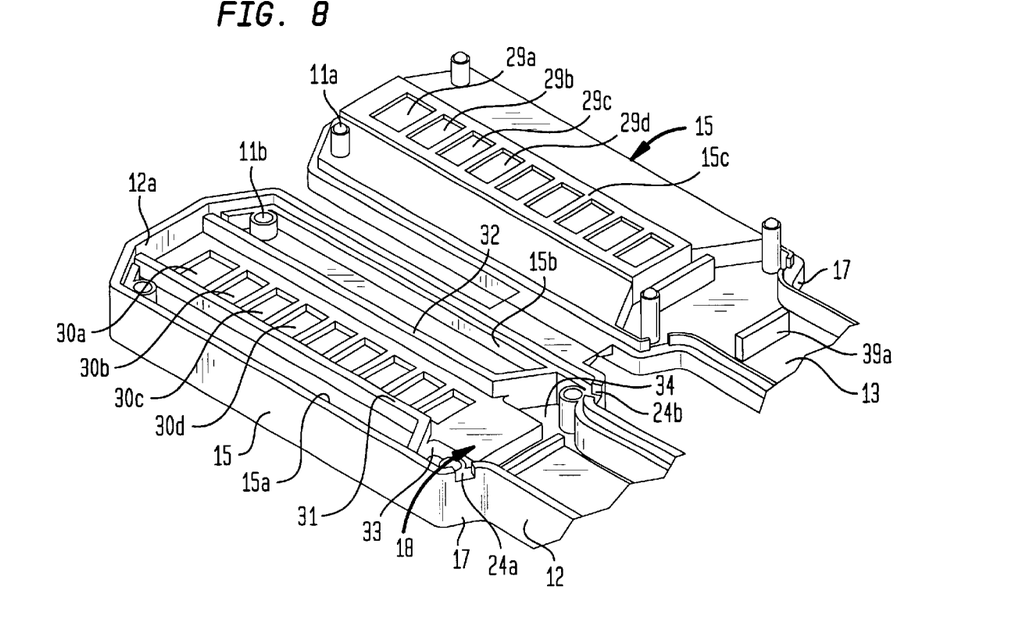
FIG. 8 is an enlarged perspective view of the enlarged end section of the housing shown in FIG. 2 and in the open position and also showing the openings for breaking capillary flow along the sealing means for the upper and lower sections of the housing.
Figure 9:
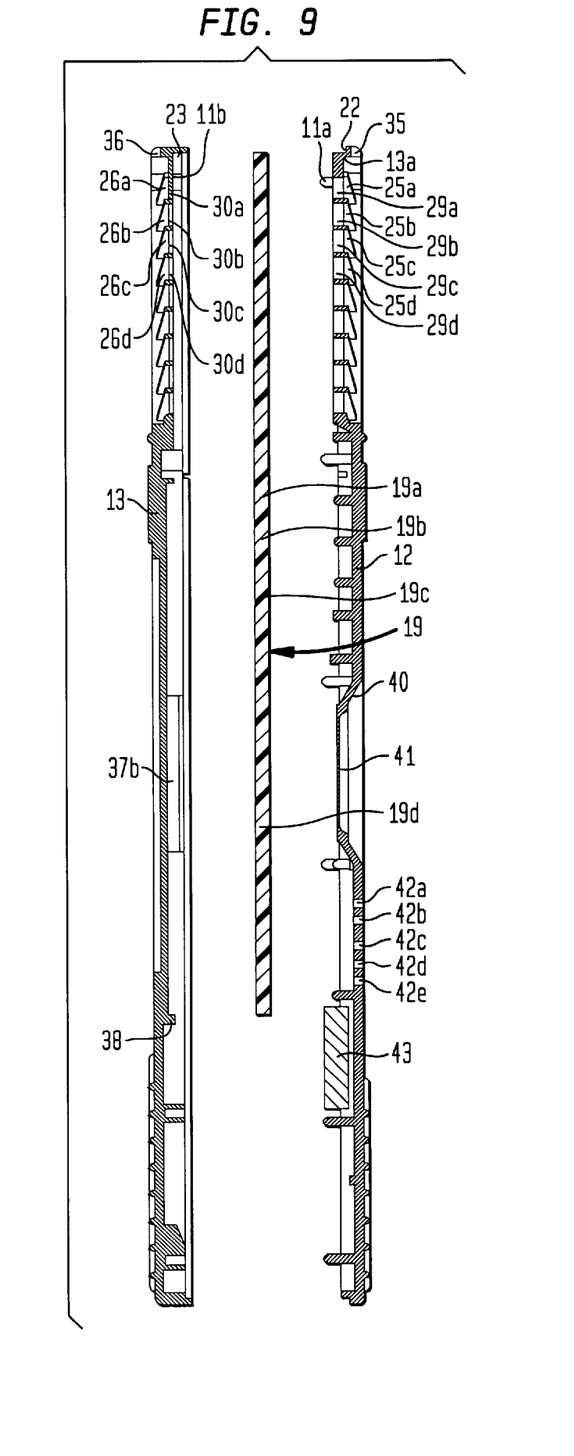
FIG. 9 is a longitudinal cross-section taken on line 9—9 of FIG. 1 with the lower section and upper section spaced from each other and the test strip separated from the test strip holding channel.
Figures 10, 11, 12, 13, 14, 15:
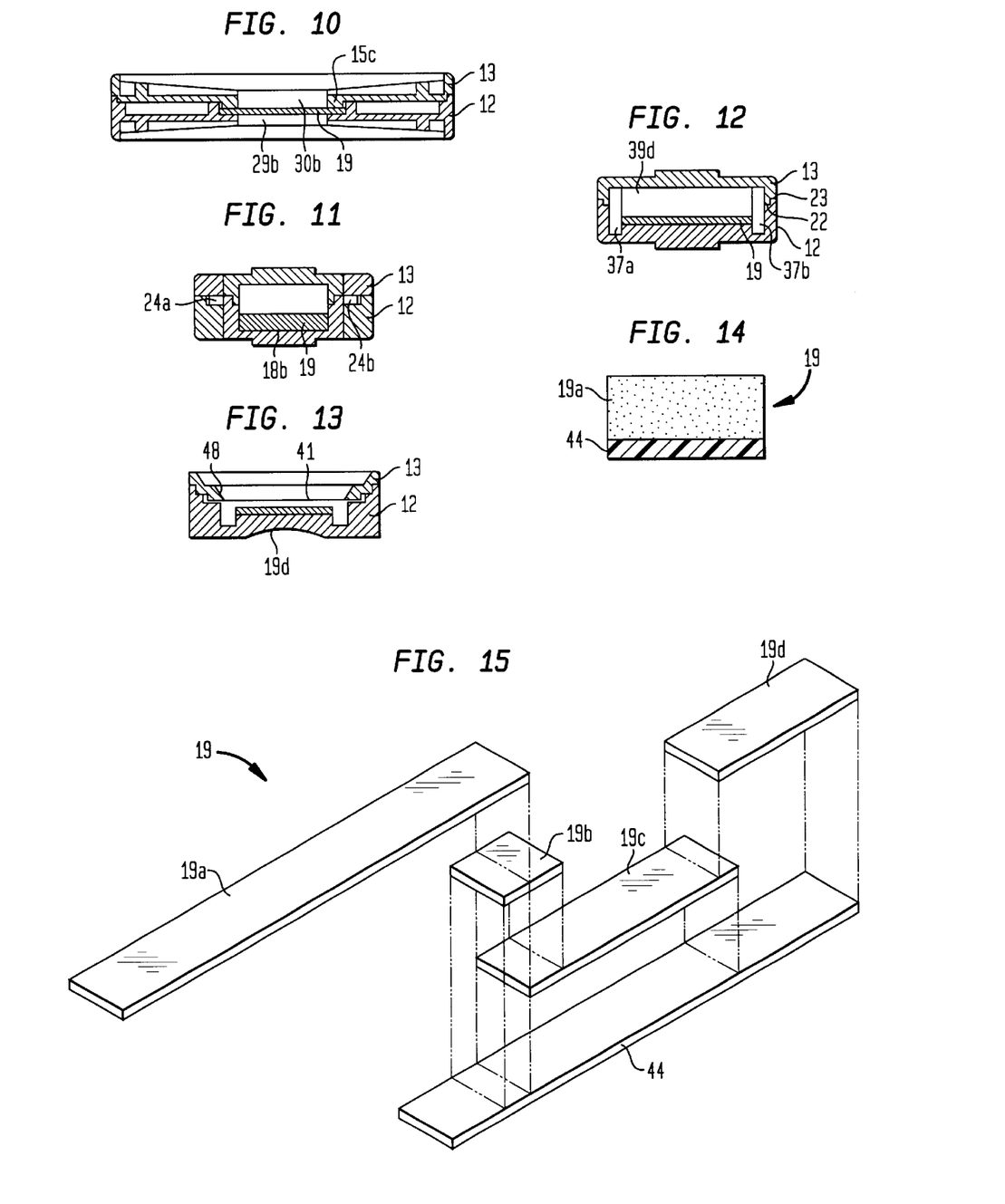
FIG. 10 is an enlarged transverse cross-section taken on line 10—10 of FIG. 1.
FIG. 11 is an enlarged transverse cross-section taken on line 11—11 of FIG. 1.
FIG. 12 is an enlarged transverse cross-section taken on line 12—12 of FIG. 1.
FIG. 13 is an enlarged transverse cross-section taken on line 13—13 of FIG. 1.
FIG. 14 is an enlarged transverse cross-section of the test strip taken on line 14—14 of FIG. 7.
FIG. 15 is an exploded view of the form of test strip shown at FIG. 7.

FIGS. 1, 7 and 9 further show that on the side of the window section 40 in the upper section 13, opposite or remote from the plurality of inwardly extending projections 39a, 39b, etc., a plurality of spaced ventilating openings 42a, 42b, 42c and 42d are provided for ventilating the interior of the handle section 16 of housing 11 when the test device 10 is in use. Ventilating the handle section 16 will remove excess moisture from the after-sol pad section 19d of the test strip, help to maintain the direction of capillary movement in the test strip of the fluid being tested and thus, increase the sensitivity of the test strip and avoid an inaccurate reading of the test result signaled by the test strip 19.

Also to decrease excessive moisture in the interior of the housing 11 without affecting the operation or interfering with the operation of the test strip, a desiccant member 43 is provided at this end of the handle section 16 of the housing 11. Desiccant member can be made of any suitable materials such as the Scavenger Preform Tablet sold by Mikesoh Telelogus, Inc of Robles, N.Y. and other similar such materials which are easily purchasable on the open market.

FIGS. 7, 9, 12, 13 and 14 show that the test strip 19 is formed with a plastic film base 44 on which are serially attached by any suitable means the sample receiving section 19a, a reagent section 19b, an intermediate transfer section 19c, and an after-sol pad section 19d. The intermediate transfer section 19c provides the signal, at the window section 40 in the housing 11, either as color or a stripe, which shows the positive or negative results for the given test based on the fluid being tested.

Test strip 19 is positioned in the test strip receiving channel 18 along the longitudinal length of the housing 11 so that the after-sol pad section 19d in assembled position is disposed at a point beyond the window section in the housing 1 at a point for operative association with the spaced ventilating openings 42a, 42b, 42c and 42d to enable excess moisture in the after-sol pad to escape from the interior of the housing, all as shown in FIGS. 1, 7, 9 and 13 of the drawings.

Plastic film base 44 is made of relatively thin vinyl plastic or the like synthetic material. Affixed to one end of the upper face of the plastic film base 44 by any suitable means is the elongated sample collection member 19a of the test strip 19. Sample collection member 19a is made of a highly absorbent matrix material such as very thin fiber glass which will saturate easily when brought into contact with the fluid being tested. Thus, when the test strip 19 is placed in the test strip holding section 18 in the housing 11, the plastic film base 44 is positioned so that the sample collection member 19a will extend into the enlarged end section for operative coaction with inlet ports or openings 29a, 29b, 29c and 29d in the lower section 12 and inlet ports or openings 30a, 30b, 30c and 30d in the upper section 13 of the housing, all as above described. The characteristics of the material from which the sample collection member 19a of the test strip 19 determine the degree and capacity for absorption of the fluid to be tested by the sample collection member 19a and the relative size of the inlet ports or openings will act to provide a sufficient quantity of the fluid to be tested for such absorption by the sample collecting member 19a of the test strip 19. This absorbed fluid then travels by capillary action through the remaining sections of the test strip 19. The housing 11 is so designed that the directional movement by such capillary action in the test strip 19 of the fluid being tested is maintained and enhanced.

At the same end where the sample collection member 19a is connected to the plastic film base, a reagent pad 19b is also connected. Reagent pad 19b is also made of a highly absorbent material having a predried reagent randomly dispersed therethrough which is mixed and dissolved in the fluid being tested as it moves through the test strip by capillary action. At the opposite end of the reagent pad 19b, communicates with one end of an intermediate transfer member 19c affixed to the outer face of the plastic film 19a. Intermediate transfer member 19c made of a microporous membrane material such as a nitrocellulous material which materials are also purchasable on the open market. Since sample collection member 19a, the reagent pad 19b and the intermediate transfer member 19c are in communication with each other, as the fluid to be tested moves by capillary action through the test strip 19, it will mix with and dissolve the reagent dispersed in the reagent pad and react therewith. When this mixture moves through the intermediate transfer member 19c the result for which the fluid is being tested is established and such result becomes visible through the window section 40 of the housing 11.

At the end of the intermediate transfer member 19c remote from the sample collecting member 19a and the reagent pad 19b, an after-sol member 19d communicates with and is connected to the intermediate transfer section 19c and the plastic film base 44 so that when the test strip 19 is in assembled position, it extends past the viewing window 40. The after-sol member is formed from a highly absorbent material such as tissue paper, whatman grade 8-½, also available on the open market, and the reacted fluid will therefore continue to flow by capillary action through the intermediate transfer member 19c signal, as by a color change or color line, the results, if any, of the physical condition for which the fluid sample is being tested.

The reagents for testing for a given physical condition which are dissolved in the fluid being tested are well known in the art and therefore are known to those skilled in the art and will not be more fully described herein.

Accordingly, a relatively simple single-use testing device has been above described with an enclosed test strip, in which the number of parts for the housing are reduced, thus reducing the labor and cost for manufacturing the housing, provides an improved structure and operation for a testing device which avoids the prior art hydraulic pressure problem of excess flooding in the interior of the housing for the testing device, maintains good capillary action in the test strip, and provides signals and results which are constant and accurate.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A testing device for detecting a physical condition from a fluid specimen or stream to be tested comprising:
   a. a housing movable from an open to a closed position and vice versa having, a test strip therein,
   b. an enlarged end section on said housing for receiving and capturing at least a portion of the fluid to be tested has, inlet port means occluded by and coacting with one end of the test strip to permit a predetermined quantity of fluid to be absorbed by this associated end of the test strip, and
   c. said housing having, a viewing window for reading the results, if any, signaled by the test strip during use of the test device.

2. A testing device for detecting a physical condition from a fluid specimen or stream to be tested comprising:
   a. a housing movable from an open to a closed position and vice versa having, a test strip therein,
   b. an enlarged end section on said housing for receiving and capturing at least a portion of the fluid to be tested has, inlet port means occluded by and coacting with one end of the test strip to permit a predetermined quantity of fluid to be absorbed by this associated end of the test strip,
   c. means on the enlarged end section to enable excess fluid to overflow off the enlarged end section, and
   d. said housing having, a viewing window for reading the results, if any, signaled by the test strip during use of the test device.

3. A testing device for detecting a physical condition from a fluid specimen or stream to be tested, comprising:
   a. a housing movable from an open to a closed position and vice versa and having, a test strip holding channel, and a test strip mounted in said test strip holding channel in the housing,
   b. an enlarged end section on said housing for communication with the fluid to be tested has, inlet port means, and said inlet port means occluded by and coacting with one end of the test strip in assembled position to permit a predetermined amount of fluid to be absorbed by this associated end of the test strip,
   c. means for sealing the housing in the closed position including, means to limit capillary action of the fluid along the sealing means to prevent contamination of the test strip during use of the testing device, and
   d. said housing having, a viewing window for reading the results, if any, signaled by the test strip during use of the test device.

4. In a testing device as in claims 1, 2 or 3 wherein the inlet port means includes:
   a. at least one opening in the enlarged end section disposed for coaction with the test strip when in assembled position in the housing, and
   b. said test strip made of a highly absorbent material and in assembled position in said strip holding channel when the housing is in the closed position disposed to occlude the at least one opening to prevent the fluid being tested from flooding into the housing.

5. In a testing device as in claims 1, 2 or 3 wherein the enlarged end section includes:
   a. at least one operatively associated pair of transverse partitions defining, a sized transverse guide channel therebetween for catching and holding a predetermined quantity of the fluid to be tested when the testing device is being used, and b. said guide channel having, the inlet port means therein disposed for coaction with the test strip.

6. In a testing device as in claims 1, 2 or 3 wherein the enlarged end section is sized and shaped to provide at least one substantially large surface area for contact with the fluid to be tested.

7. In the testing device as in claim 2 wherein the means to enable excess fluid to be tested to overflow off the enlarged end section is at least one sized and shaped outlet disposed on the exterior of the enlarged end section.

8. In the testing device as in claim 2 wherein the means to enable excess fluid to overflow off the enlarged end section includes:

a. an end wall formed on the exterior of the enlarged end section, and b. at least one sized and shaped outlet formed in the end wall disposed when the test device is in use for communication with the fluid to be tested to permit said fluid to overflow off of the housing.

9. In a testing device as in claims 1, 2 or 3 wherein the housing has a plurality of vent openings to allow excess moisture to escape from the interior of the housing to insure continuing capillary action in the test strip and prevent the test strip and viewing window from becoming blurred during operation of the testing device.

10. In a testing device as in claims 1, 2 or 3 where the housing includes:

a. at least one vent opening on the side of the viewing window opposite from the enlarged end section to allow excess moisture to escape from the interior of the housing, b. a desiccant in the housing to absorb excess moisture, and c. said vent openings and the desiccant coacting with each other to maintain the test strip and viewing window clear during operation of the testing device.

11. In a testing device as in claims 1, 2 or 3 wherein the housing includes, a plurality of test strip holding projections for operatively maintaining the test strip in assembled position when the housing is in the closed position.

12. In the testing device as in claims 1, 2 or 3 wherein the housing is fabricated from a plastic material.

13. In a testing device as in claims 1, 2 or 3 wherein the housing is fabricated from a plastic material from the group polypropylene and polyethylene.

14. In the testing device as in claim 3 wherein the means for limiting capillary action of the fluid to be tested along the sealing means is at least one opening in the line of the sealing means extending from the interior to the exterior of the housing.

15. In the testing device as in claim 3 wherein the means for limiting capillary action of the fluid to be tested along the sealing means comprises, spaced openings in the line of the sealing means on opposite sides of the housing, said openings extending from the interior to the exterior of the housing.

16. A testing device for detecting a physical condition from a fluid specimen to be tested comprising:

a. a housing having a first lower section and a coacting and matching upper section operatively connected for movement from an open to a closed position and vice versa, test strip holding channel, and a test strip in said test strip holding channel when in assembled position in the housing, b. an enlarged sized and shaped end section on said housing for communication with the fluid to be tested has, inlet port means occluded by and disposed for operative coaction with the test strip to permit a predetermined quantity of fluid to be tested to be absorbed by one end of the test strip, and means to enable excess fluid to overflow off of the enlarged sized and shaped end section, c. means for sealing the lower section and coacting and matching upper section in the closed position including, means to limit capillary action of the fluid along the sealing means to prevent contamination of the test strip and the testing device during use of the testing device, and d. said housing having, a viewing window for reading the results, if any, signaled by the test strip during use of the test device.

17. A housing for a test device with a test strip therein comprising:

a. generally elongated housing means including, a first shaped section, and a matching second shaped section operatively connected to each other for movement from an open to a closed position, a longitudinally extending test strip holding channel, and a test strip mounted in said test strip holding channel when the housing is in the closed position, b. said elongated housing means having, an enlarged sized and shaped section at one end for receiving a fluid specimen, and means forming an overflow section on said end section to enable excess fluid to flow off the end section, c. said enlarged sized and shaped end section having a plurality of transversely and serially disposed guide channels on at least one surface of the housing, and sized fluid inlet ports in each of said channels extending through the surface of the housing, d. said inlet ports occluded by and disposed for operative coaction with said test strip to permit a predetermined quantity of the fluid to come into contact with and be absorbed by the test strip, e. sealing means between the first shaped section and the operatively connected and matching second shaped section to seal the housing against fluid penetration when the housing is in the closed position, f. means for limiting capillary action of the fluid being tested flowing along the sealing means, and g. said housing having, a viewing window for reading the results, if any, signaled by the test strip during use of the test device.

18. In the housing for a testing device as in claims 14 and or 15 wherein the means for limiting capillary action by the fluid specimen to be tested along the sealing means is at least one opening in the sealing means extending from the interior to the exterior of the housing.

19. In the housing for a testing device as in claims 14 and or 15 including, a. venting openings in the housing on the side of the viewing window opposite form the enlarged end section, b. a desiccant disposed in said housing, and c. said venting openings and said desiccant to absorb excess moisture in the interior of the housing to improve continuity of capillary action in the test strip and to maintain the test strip and viewing window clear.

20. In a test device as in claims 1, 2 or 3 wherein the viewing window in the housing includes, means for sealing the viewing window.

* * * * *

UNITED STATES PATENT AND TRADEMARK OFFICE
CERTIFICATE OF CORRECTION

PATENT NO. : 6,740,293 B1
DATED : May 25, 2004
INVENTOR(S) : Fangling Deng

It is certified that error appears in the above-identified patent and that said Letters Patent is hereby corrected as shown below:

Column 12,
Lines 9-55, delete claims 1-3 and insert therefor claims 1-3 as follows:

--1. A testing device for detecting a physical condition from a fluid specimen or stream to be tested comprising:
    a.    an elongated housing means having a test strip section, and a matching cover section pivotally connected to the test strip section and movable from open to closed position, and a test strip mounted along the longitudinal length of said test strip section,
    b.    said test strip section and said cover section of the housing means shaped to form, a handle, an enlarged specimen receiving end continuous with the handle, and said specimen receiving end at least twice the width of the handle to provide a greater area of contact for the fluid specimen,
    c.    said enlarged specimen receiving end of the testing device having a plurality of centrally disposed openings, a plurality of spaced transversely disposed partitions defining a corresponding plurality of guide channels therebetween respectively communicating with an associated one of the plurality of centrally disposed inlet openings, and said guide channels sized to trap a predetermined quantity of the fluid specimen to be tested,
    d.    said plurality of inlet openings occluded by and coacting with one associated end of the test strip to enable a predetermined quantity of the fluid specimen to be absorbed by this end of the test strip, and
    e.    said housing having a viewing window for reading the results, if any, signaled by the test strip during use of the testing device.

2. A testing device for detecting a physical condition from a fluid specimen or stream to be tested comprising:
    a.    an elongated housing means having a test strip section, and a matching cover section pivotally connected to the test strip section and movable from open to closed position, and a test strip mounted along the longitudinal length of said test strip section,
    b.    said test strip section and said cover section of the housing means shaped to form, a handle, an enlarged specimen receiving end continuous with the handle, and said specimen receiving end at least twice the width of the handle to provide a greater area of contact for the fluid specimen,
    c.    said enlarged specimen receiving end of the testing device having a plurality of centrally disposed openings, a plurality of spaced transversely disposed partitions defining a corresponding plurality of guide channels therebetween respectively communicating with an associated one of the plurality of centrally disposed inlet openings, and said guide channels sized to trap a predetermined quantity of the fluid specimen to be tested,
    d.    said plurality of inlet openings occluded by and coacting with one associated end of the test strip to enable a predetermined quantity of the fluid specimen to be absorbed by this end of the test strip,
    e.    means on the enlarged specimen receiving end to enable excess fluid to overflow off the enlarged specimen receiving end, and
    f.    said housing having a viewing window for reading the results, if any, signaled by the test strip during use of the testing device.
    3. A testing device for detecting a physical condition from a fluid specimen or stream to be tested comprising:
    a.    en elongated housing means having a test strip section, and a matching cover section pivotally connected to the test strip section and movable from open to closed position, and a test strip mounted along the longitudinal length of said test strip section,
    b.    said test strip section and said cover section of the housing means shaped to form, a handle, an enlarged specimen receiving end continuous with the handle, and said specimen receiving end at least twice the width of the handle to provide a greater area of contact for the fluid specimen,

UNITED STATES PATENT AND TRADEMARK OFFICE
CERTIFICATE OF CORRECTION

PATENT NO. : 6,740,293 B1
DATED : May 25, 2004
INVENTOR(S) : Fangling Deng

It is certified that error appears in the above-identified patent and that said Letters Patent is hereby corrected as shown below:

Column 12 (cont'd), c. said enlarged specimen receiving end of the testing device having a plurality of centrally disposed openings, a plurality of spaced transversely disposed partitions defining a corresponding plurality of guide channels therebetween respectively communicating with an associated one of the plurality of centrally disposed inlet openings, and said guide channels sized to trap a predetermined quantity of the fluid specimen to be tested,     d. said plurality of inlet openings occluded by and coacting with one associated end of the test strip to enable a predetermined quantity of the fluid specimen to be absorbed by this end of the test strip,     e. means for sealing the housing in the closed position including means to limit capillary action of the fluid specimen along the sealing means to prevent contamination of the test strip during use of the testing device, and     f. said housing having a viewing window for reading the results, if any, signaled by the test strip during use of the testing device.--

Column 13, line 60 - Column 14, line 48,
Delete claims 16-17 and insert therefor claims 16-17 as follows:

--16. A testing device for detecting a physical condition from a fluid specimen to be tested comprising:

a. an elongated housing means having a lower section, and a matching cover section operatively connected for movement from an open to a closed position and vice versa, a test strip holding channel in said lower section, and a test strip in assembled position mounted along the longitudinal length of said test strip holding channel,     b. said upper section and said cover section of the housing means shaped to form, a handle, an enlarged specimen receiving end continuous with the handle, and said specimen receiving end at least twice the width of the handle to provide a greater area of contact for the fluid specimen,     c. said enlarged specimen receiving end of the testing device disposed for communication with the fluid specimen to be tested and having, a plurality of centrally disposed inlet ports, a plurality of spaced transversely disposed partitions defining a corresponding plurality of guide channels therebetween respectively communicating with an associated one of the plurality of centrally disposed inlet ports, and said guide channels sized to trap a predetermined quantity of the fluid specimen to be tested,     d. said plurality of inlet openings occluded by and coacting with one associated end of the test strip to enable a predetermined quantity of the fluid specimen to be absorbed by this end of the test strip,     e. means to enable excess fluid to be tested to overflow off of the enlarged specimen receiving end of the testing device,     f. means for sealing the lower section and coacting and matching cover section in the closed position including, means to limit the capillary action of the fluid specimen along the sealing means to prevent contamination of the test strip and the testing device during use of the testing device, and     g. said housing having a viewing window in the handle and remote from the enlarged specimen receiving end for reading the results, if any, signaled by the test strip during use of the testing device.--

17. A housing for a test device with a test strip therein for detecting a physical condition from a fluid specimen or stream to be tested comprising:

a. said housing generally elongated and including, a first shaped section, and a matching second shaped section operatively connected to each other for movement from open to closed position, a longitudinally extending test strip holding channel, and said test strip mounted along the longitudinal length of said test strip holding channel when the housing is in the closed position for testing,     b. said first section and said second section of the housing shaped to form a handle, an enlarged specimen receiving end continuous with the handle, said specimen receiving end at least ,twice the width of the handle to provide a greater area of contact for the fluid specimen, and means forming an overflow device on at least one of said enlarged specimen receiving ends to enable excess fluid specimen to be tested to flow off said at least one specimen receiving end,     c. said at least one enlarged specimen receiving end of the testing device having a plurality of centrally disposed inlet openings disposed for communication with the test strip holding channel, a plurality of spaced transversely disposed partitions defining a corresponding plurality of guide channels therebetween respectively communicating with an associated one of the plurality of centrally disposed inlet openings, and said guide channels sized to trap a predetermined quantity of the fluid specimen to be tested,

UNITED STATES PATENT AND TRADEMARK OFFICE
CERTIFICATE OF CORRECTION

PATENT NO. : 6,740,293 B1
DATED : May 25, 2004
INVENTOR(S) : Fangling Deng

It is certified that error appears in the above-identified patent and that said Letters Patent is hereby corrected as shown below:

Column 13, line 60 - Column 14, line 48 (cont'd), d.    said plurality of inlet openings occluded by and coacting with one associated end of the test strip in assembled position in the test strip holding channel to enable a predetermined quantity of the fluid specimen to be absorbed by this end of the test strip, e.    means for sealing the first section and coacting and matching second section in the closed position including, means to limit the capillary action of the fluid specimen along the sealing means to prevent contamination of the test strip and the testing device during use of the testing device, and     f.    said housing having a viewing window remote from the specimen receiving end for reading the results, if any, signaled by the test strip during use of the testing device.--

Column 14,
Lines 48 and 53, delete "14" and insert therefor -- 16 --.
Lines 49 and 54, delete "15" and insert therefor -- 17 --.

Signed and Sealed this

Seventh Day of September, 2004

JON W. DUDAS
*Director of the United States Patent and Trademark Office*